United States Patent
Van Cromvoirt et al.

Patent Number: 6,065,470
Date of Patent: May 23, 2000

[54] NOSTRIL DILATOR

[76] Inventors: Lambertus Adrianus Van Cromvoirt, Paulus Potter Plein 1, 5171 XJ Kaatsheuvel; Josephus Wouterus Clemens Maria Van Beurden, Gruegstraat 36, 5011 HP Tilburg, both of Netherlands; Eric Henri Louis Van Pottelbergh, Overbeekstraat 20, B-3450 Geetbets; Luc Albert Guido Gilis, Schoolstraat 30, B-2430 Laakdal, both of Belgium

[21] Appl. No.: 08/947,933

[22] Filed: Oct. 9, 1997

Related U.S. Application Data

[63] Continuation-in-part of application No. 08/936,126, Sep. 24, 1997.

[51] Int. Cl.[7] .................................................. A61M 15/00
[52] U.S. Cl. ............... 128/200.24; 606/199; 606/204.45
[58] Field of Search .................. 128/200.24, 207.19; 606/199, 204.45; 528/502.13

[56] References Cited

U.S. PATENT DOCUMENTS

| | | |
|---|---|---|
| Re. 35,408 | 12/1996 | Petruson . |
| D. 310,565 | 9/1990 | Petruson . |
| D. 379,513 | 5/1997 | Ierulli . |
| D. 380,264 | 6/1997 | Petruson . |
| 1,292,083 | 6/1919 | Sawyer . |
| 3,426,751 | 2/1969 | Radewan . |
| 4,340,040 | 7/1982 | Straith . |
| 5,476,091 | 12/1995 | Johnson . |
| 5,533,499 | 7/1996 | Johnson . |
| 5,533,503 | 7/1996 | Doubek et al. . |
| 5,546,929 | 8/1996 | Muchin . |
| 5,549,103 | 8/1996 | Johnson . |
| 5,553,605 | 9/1996 | Muchin . |
| 5,611,333 | 3/1997 | Johnson . |
| 5,611,334 | 3/1997 | Muchin . |
| 5,653,224 | 8/1997 | Johnson . |

FOREIGN PATENT DOCUMENTS

| | | |
|---|---|---|
| 1004239 | 10/1996 | Netherlands . |
| WO 92/22340 | 12/1992 | WIPO . |
| WO 94/23675 | 10/1994 | WIPO . |
| WO 96/01093 | 1/1996 | WIPO . |

OTHER PUBLICATIONS

"Breathe Right" ™ article/advertisement ©1994 CNS, Inc. brochure #6100–643–001, 6100–607–001 & –002 (5 pages).

*Primary Examiner*—Aaron J. Lewis

[57] ABSTRACT

A nostril dilator with a longitudinal shape having a first nostril holding member and a second nostril holding member located at opposing ends. Each holding member is provided with a first layer of adhesive for temporary adherence to the nostril. The nostril dilator also comprising a connecting member for joining the first and second holding members to each other and keeping them at a distance from each other. The nostril dilator also having an elastic member connected at least to the first and second holding members for drawing open the nostrils of the nose.

10 Claims, 2 Drawing Sheets

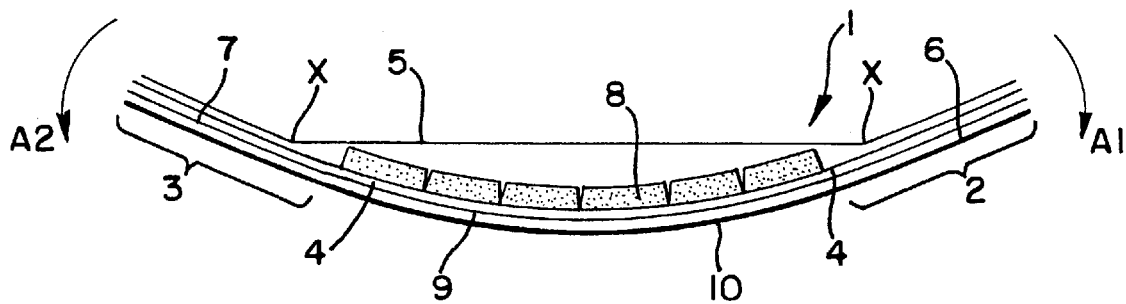
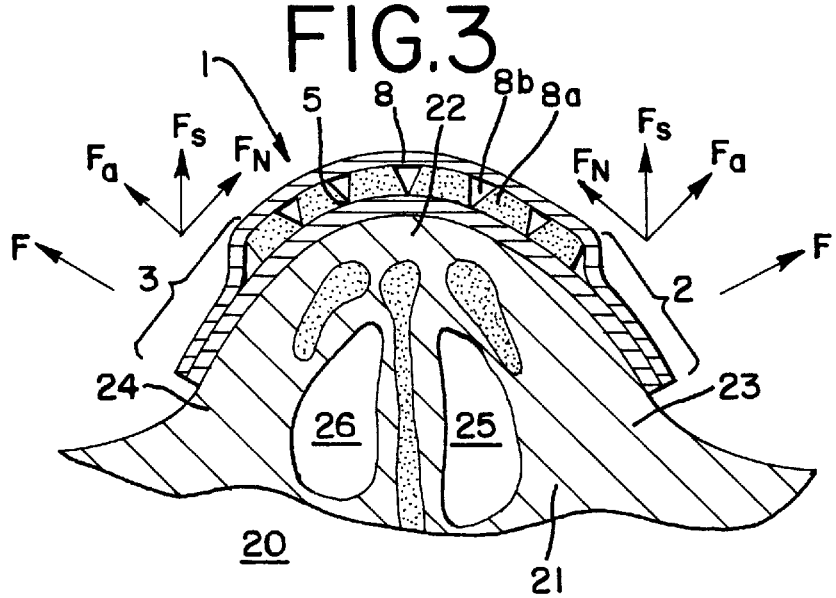

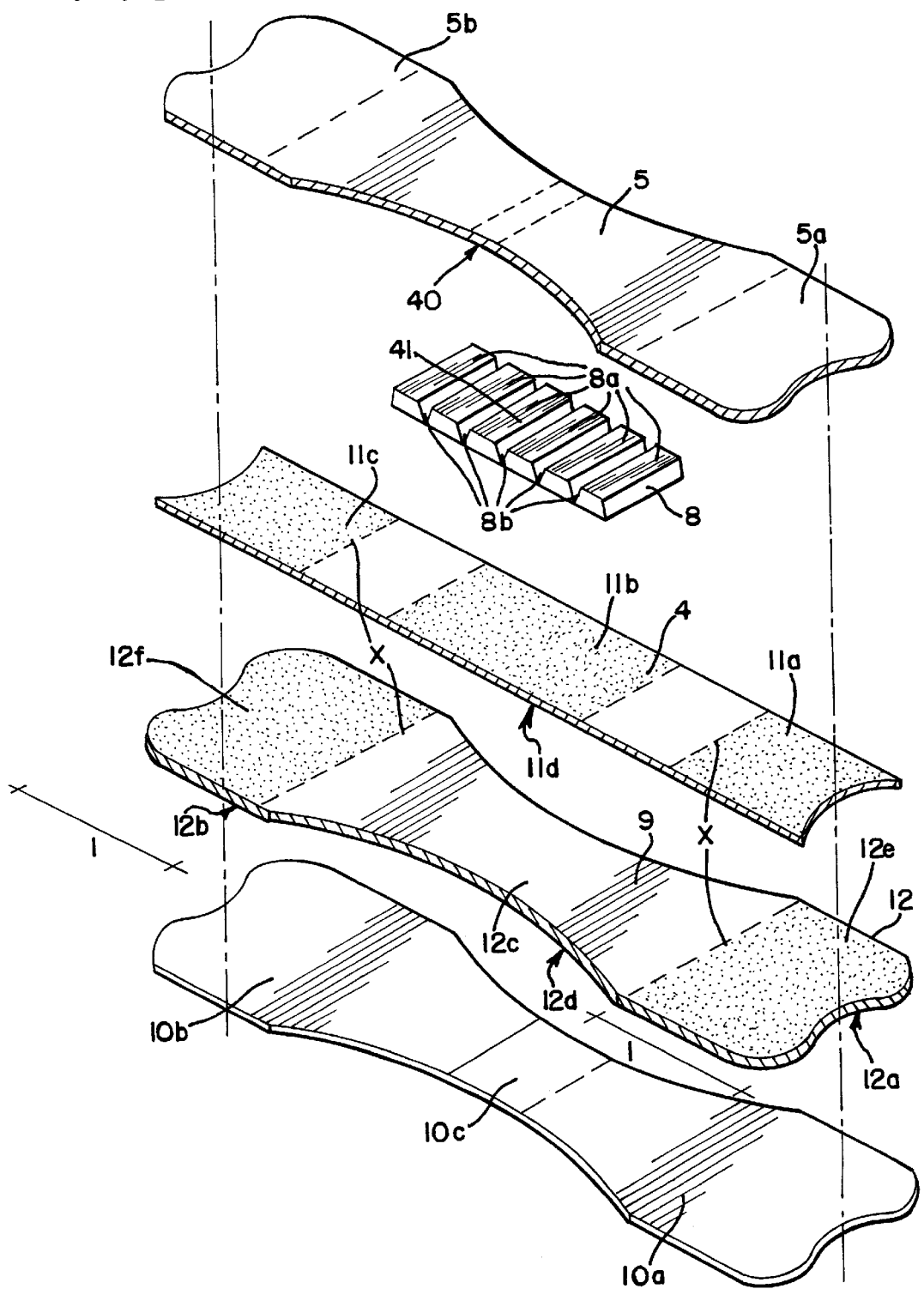

NOSTRIL DILATOR

RELATED U.S. APPLICATION DATA

This is a continuation-in-part application of U.S. application Ser. No. 08/936,126 for "Nostril Dilator", filed Sep. 24, 1997.

TECHNICAL FIELD

The invention relates to a nostril dilator for biassing the wings of the nose of the user to a position which widens the nostrils.

BACKGROUND

Nostril dilators are commonly used by people suffering from colds in order to improve breathing. The nostril dilators are used to open breathing passages even when there is mucus build up within the nose. Wearers have found that nostril dilators are particularly useful during sleep and can prevent snoring caused by partial nostril blockage.

Athletes use nostril dilators to enhance their performance. Nostril dilators allow the athlete to take increased volumes of oxygen through the nose. The increased oxygen intake improves the athlete's stamina.

U.S. Pat. No. 1,292,083, issued to Sawyer ("Sawyer"), discloses a nose expander or nostril dilator consisting of a resilient brace. The resilient brace has opposing ends. Each end is provided with a hooklet. Disk-shaped cushions which are provided with an adhesive layer for adhesion to the nostrils can be attached to the hooklets. In use, the resilient brace is flexed and positioned over the bridge of the nose, and the disk-shaped cushions are applied to each nostril. The tendency of the resilient brace to return to its pre-flexed shape results in outwardly directed forces applied perpendicularly to the nostrils via the cushions, whereby the nostrils are flared.

U.S. Pat. No. 1,950,839, issued to Chirila ("Chirila"), also discloses a nostril dilator. This nostril dilator also comprises a brace having spring-loaded suction cups mounted on opposing ends. The nostril dilator of Chirila functions in essentially the same manner as the nostril dilator of Sawyer.

More recently, nostril dilators have been disclosed in international patent applications WO 92/22340, WO 94/23775 and WO 96/01093 and the German Utility Model 94.11494. These nostril dilators include a plaster having a flat, relatively stiff strip of elastically flexible material within the plaster. In principle, these nostril dilators function in the same manner as Sawyer and Chirila. The flat, relatively stiff strip of elastically flexible material is flexed over the bridge of the nose. End areas are adhered to either nostril. The nostrils are pulled open by the restoring forces present in the flat, relatively stiff strip of elastically flexible material.

While the above-referenced nose dilators improve breathing, the human nose is a sensitive organ, and these nose dilators apply forces on the nose which are often uncomfortable to the user. These nostril dilators rely on a rather stiff and rigid bendable member. In particular, when this member is touched during sleep or touched unintentionally during the day, they can exert irritating forces on the nose of the user.

The present invention is designed to overcome this problem while maintaining the improvement in breathing.

SUMMARY OF THE INVENTION

The present invention provides a nostril dilator designed to improve the wearer's breathing with increased comfort. This invention comprises a nostril dilator having a longitudinal shape. First and second holding members are positioned at opposing ends of the dilator. Each holding member is provided with a first layer of adhesive for temporarily adhering the holding members to the nostril. A connecting member joins the first and second holding members and keeps them at a distance from each other. An elastic member extends between the first and the second holding members on the side of the connecting member facing away from the nose. The elastic member has end areas which join the elastic member to the first and second holding members. The elastic member is formed by a layer which is, at least in a longitudinal direction, elastic, and which is separate from the connecting member at least in the area between a central transverse area of the nostril dilator and both end areas situated on both sides thereof.

By keeping the connecting member and the elastic member separate from each other, these two elements can shift in relation to each other, whereby the nostril dilator is more compliant in that area and reallocation of forces is promoted. As a consequence, the wearer's comfort will increase.

Preferably, in an unloaded state, the elastic member has a length between the holding members which is smaller than that of the connecting member between both holding members. Consequently, when applying the nostril dilator, the elastic member can be stretched to the length of the connecting member. In so doing a large tensile force is attainable.

The elastic member is preferably manufactured from a layer of elastic synthetic material, preferably a layer of polyurethane film. Such films can be printable, so that advertisements, names, etc. can be applied to the nostril dilator.

Another advantage of such an elastic synthetic material is that the latter displays relaxation behavior. As a result the tensile force decreases somewhat over time, and thus, the force on the nose decreases. However, the force on the nose does not decrease to an extent where the nostril dilator does not function properly.

This synthetic elastic material's relaxation behavior helps avoid damage to the nose tissue. When the nostril dilator is applied to the nose, the muscle cells in the nose are slightly extended. This causes a fluid to flow between the muscle cells and an under pressure forms there. As a result, the muscles of the nose weaken and the nostrils are extended further outward. Over time, this is harmful to the muscle fibers of the nose which become loaded to a maximum elongation. The relaxing nature of the elastic member helps prevent this.

Moreover, the position of elastic member in relation to the remainder of the nostril dilator and, in particular, the holding members, can be selected during manufacture. As a result, while using the same material and the same cross section of the elastic member, the tensile force can be altered to make the nostril dilator suitable for one target group (people in their twenties, for instance) or another target group (elderly people). This same improvement allows flexibility in the distributing the stresses along the holding members.

In another embodiment, the elastic member is separated from the connecting member over the area between its end areas.

In another embodiment, the elastic member is directly or indirectly connected to the connecting member in the central transverse area, which is preferably very narrow. The elastic member cannot be asymmetrically stretched over the nose when the nostril dilator is not applied to the nose in a symmetrical fashion.

In yet another embodiment, the nostril dilator includes a spacing member between the elastic member and the connecting member. The spacing member keeps the tensile member and the connecting member at a distance from one another. The spacing member increases the distance over which the elastic member is stretched and introduces a force having a direct component perpendicular to the direction of the holding member and away from the nose. The spacing member allows the connecting member to be made thinner and, thus, flexurally slack which, in turn, leads to greater comfort.

Preferably, the spacing member is removably adhered to the nostril dilator. This allows the user to remove the spacing member and replace it with another thicker or thinner spacing member so as to adjust the tensile forces to his/her needs. In addition, the spacing member can be divided in the longitudinal direction of the nostril dilator, so that the length and the slope of the elastic member can be altered.

Another aspect of the invention provides a nostril dilator having an optical or physical positioning means or pilot means. The positioning means aids the user in placing the nostril dilator correctly over the bridge of the nose. Preferably, the positioning means is formed by a discontinuity in a direction perpendicular to the main plane of the nostril dilator. To this end the spacing member can, at least at the location of the longitudinal center of the nostril dilator, be provided with a narrower width. When applying the nostril dilator to the nose, the discontinuity or region of narrower width is placed over the bridge of the nose.

The positioning means can also be achieved by narrowing the connecting member in the region of its longitudinal center.

In yet another embodiment, cushions are placed between the central transverse area and the holding members. The cushions contact the nostrils on both side of the bridge of the nose to increase comfort.

Other advantages and aspects of the present invention will become apparent upon reading the following description of the drawings and detailed description of the invention.

BRIEF DESCRIPTION OF THE DRAWINGS

FIG. 1 shows a side view of a nostril dilator according to the invention;

FIG. 2 shows the nostril dilator of FIG. 1, in an exploded view; and,

FIG. 3 shows a cross-section through the nose of the user with the nostril dilator according to the invention placed thereon.

DETAILED DESCRIPTION

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

The nostril dilator 1 shown in FIG. 1 comprises holding members 2, 3. The holding members 2, 3 have holding member surfaces 6, 7 which are provided with a layer of suitable biocompatible, breathing adhesive for adhesion to the nose. A connecting member 4 extends between the holding members 2, 3. An elastic layer 5 also extends between the holding members 2, 3. The elastic layer 5 has a length between the holding members 2, 3 which is shorter than the length of the connecting member along the same course. This arrangement causes the connecting member 4 to be concave towards the elastic layer 5 and convex toward the nose.

The nostril dilator of FIG. 1 further comprises a spacing strip 8. The spacing strip 8 is positioned between the elastic layer 5 and the connecting member 4.

FIG. 3 shows the nostril dilator 1 in use on a human nose. The elastic layer 5 is the outer layer of the nostril dilator 1. The elastic layer 5 is generally produced from a polyurethane foil. The elastic layer 5 has a thickness of approximately 120 $\mu$m, more preferably 120–145 $\mu$m, and most preferably 145 $\mu$m, or any range or combination of ranges therein. The elastic layer 5 has a weight of approximately 56 $g/m^2$, more preferably 56–63 $g/m^2$, and most preferably 63 $g/m^2$, or any range or combination ranges therein. An elastic layer 5 produced from a polyurethane foil to a thickness of 25 mm will have an elongation of 9–11% at a force of 5 N. This same elastic layer 5 will have an elongation of 500–600% at a breaking force of 39–42 N. Polyurethane foil is particularly useful in producing the elastic layer 5 because it has breathing properties which increase the wearer's comfort.

Referring to FIG. 2, the spacing strip 8 is divided into a plurality of ribbons 8a by deep notches or slits 8b. The ribbons 8a are hingedly attached to one another and possibly detachable from one another. The spacing strip 8 is preferably produced from a polymeric material, preferably a polyethylene foam foil. The spacing strip 8 preferably has a thickness of 2 mm, a length of 24 mm, and a width of 9–10 mm.

The connecting member 4 is a relatively pressure resistant yet flexurally slack strip. The connecting member 4 is preferably produced from a polymeric material such as a polyester and has a thickness of 125 $\mu$m and a width of 9–10 mm. The connecting member 4 can extend the entire length of the nostril dilator 1; however, in the preferred embodiment, the connecting member 4 is somewhat shorter in length than the nostril dilator 1 to enhance the comfort to the wearer. The connecting member 4 limits the extent to which the elastic layer 5 can be stretched, and accommodates the pressure resulting from the tension in the taut elastic layer 5.

The connecting member 4 has outer adhesive layers 11a, 11c provided on end areas and a central adhesive layer 11b located on a central region. The outer adhesive layers 11a, 11c serve to attach the connecting member 4 with the elastic layer 5. The central adhesive layer 11b attaches the connecting member 4 to the spacing strip 8. The spacing strip 8 fully screens the elastic layer 5 from the connecting member 4 and the central adhesive layer 11b in the central region of the nostril dilator, so that the elastic layer 5 extends unattached from the connecting member 4 between the adhesive areas 11a and 11c.

On a lower side 11d, the connecting member 4 is fully provided with a similar adhesive layer. A layer of non-woven material 9 is attached to this lower side lid of the connecting member 4. The non-woven layer 9 generally has a thickness of approximately 270 $\mu$m and is the layer of the nostril dilator 1 that actually comes into contact with the nose. On a nasal side 12d, the non-woven layer 9 has two non-woven end areas 12a, 12b which are provided with a suitable adhesive layer for attachment to the wings of the nose. These non-woven end areas 12a, 12b determine the surface area of the holding members 2, 3.

On its top surface, the non-woven layer 9 is provided with an adhesive layer in two non-woven upper end areas 12e, 12f. The adhesive on the two adhesive non-woven upper end areas 12e, 12f join the non-woven layer 9 to the lower side lid of the connecting member 4 and elastic end areas 5a, 5b of the elastic layer 5. Adhesive may or may not be applied to the central region 12c of the non-woven layer 9. When no adhesive is applied to this central region 12c of the non-woven layer 9, the elastic layer 5 remains unattached from the connecting member 4 and the non-woven layer 9 in the central region 12c.

Finally, prior to use the adhesive non-woven layers 12a, 12b of the non-woven layer 9 facing toward the nose are covered by a pair of adhesive covering strips 10a, 10b produced from a paper having a weight of 55 g/m², more preferably 55–90 g/m², and most preferably 90 g/m², or any range or combination of ranges therein. These adhesive covering strips 10a, 10b are siliconized on one side. The adhesive covering strips 10a and 10b can overlap each other at a middle section 10c, so as to be easily handled by the user for removal thereof.

In the preferred embodiment, one elastic end area 5a is joined to one connecting member adhesive layer 11a and one adhesive-covered non-woven upper end area 12e. On an opposing end, the other elastic end area 5b is joined to another connecting member adhesive layer 11c and another adhesive-covered non-woven upper end area 12f. The two non-woven end areas 12a and 12b extend with a length l toward each other, so that the inner boundaries x of the regions where the elastic layer 5 is joined with the connecting member 4 and the non-woven layer 9 is the location where the elastic layer 5 exerts its force. This location is approximately ⅔ of the length l from the outer ends of the two non-woven end area 12a and 12b.

As illustrated in FIG. 1, in the nostril dilator's 1 assembled state, the length of the elastic layer 5 between the holding members 2, 3 is 5–10% shorter than the comparable lengths of the connecting member 4 and the non-woven strip 9.

At the location of the elastic layer's center 40 the elastic layer 5 can be adhered over a narrow strip 41 to the spacing strip 8. (See FIG. 2).

FIG. 3 is a cross-section of the nostril dilator 1 as arranged on the user's nose. The nostril dilator 1 is placed on the nose 21 of the user 20, and is attached with both holding members 2, 3 on the wings of the nose 23, 24. The non-adhered portion of the elastic layer 5 extends over the bridge 22 of the nose 21.

The nostril dilator 1 of the present invention is easily placed on the user's nose 21 because the nostril dilator's 1 flexural stiffness is slight due to the thinness and flexibility of the elastic layer 5, the separation between the connecting member 4 and the elastic layer 5, the thinness of the connecting member 4, the flexibility of the non-woven layer 9, and the hinged form of the spacing strip 8.

Prior to placing the nostril dilator 1 on the nose 21, the user removes both adhesive covering strips 10a, 10b and then grips both holding members 2, 3. The central area 12c of the non-woven layer 9 is applied over the bridge 22 of the nose 21. By moving both holding members 2, 3 toward him/herself in the directions A1 and A2 (see FIG. 1), respectively, the elastic layer 5 will be tensioned. Then, the holding members 2, 3 are moved further in the directions A1 and A2 and the adhesive end layers 12a, 12b of the non-woven strip 9 abut the wings of the nose 23, 24.

In use, the elastic layer 5 is extended further and, therefore, is tensioned further, due to the presence of the spacing strip 8 between the elastic layer 5 and the connecting member 4. At the location where the elastic layer 5 extends downward from the relatively high position on the spacing strip 8 to where it lies against the connecting member 4, there will be a force vector $F_N$ along the plane of the nostril dilator 1 and a perpendicular force vector $F_Q$ applied to the holding members 2, 3 which result in a force vector $F_S$ applied to the nose 21. Thus, the nostril dilator 1 attains the character of a lattice girder. Furthermore, the force vector $F_N$ can be offset by an opposing resistive force applied by the connecting member 4. As a consequence, the wings of the nose 23, 24 will be pulled outward and the nostrils 25 and 26 are pulled open.

It is understood that, given the above description of the embodiments of the invention, various modifications may be made by one skilled in the art. Such modifications are intended to be encompassed by the claims below.

What is claimed is:

1. A nostril dilator for application to a nose having a longitudinal shape, comprising:

a first nostril holding member and a second nostril holding member, each holding member provided with a first layer of adhesive for temporary adherence to the nostril;

a connecting member for connecting the first and second holding members to each other;

an elastic member extending between the first and the second holding members on a side of the connecting member facing away from the nose and which is connected with its end areas thereto, the elastic member formed by a layer of material which is at least elastic in a longitudinal direction parallel to the longitudinal shape of the nasal dilator, and the elastic member being separate from the connecting member at least in the area between a central transverse area of the nostril dilator and both end areas situated on both sides thereof; and a spacing member which is at least in part removably adhered in the nostril dilator and positioned between the connecting member and the elastic member keeping these parts spaced, the spacing member comprising a plurality of transverse strips which are separable from one another.

2. The nostril dilator according to claim 1, wherein the elastic member is separate from the connecting member in the whole area between both its end areas.

3. The nostril dilator according to claim 1, wherein the elastic member is directly or indirectly connected to the connecting member in the central transverse area.

4. The nostril dilator according to claim 1, wherein in an unloaded state, the elastic member has a length between the holding members which is smaller than that of the connecting member between both holding members.

5. The nostril dilator according to claim 1, wherein the elastic member is produced from a polymeric material.

6. The nostril dilator according to claim 5, wherein the elastic member is formed of a printable material.

7. The nostril dilator according to claim 1, wherein at least at the location of the holding members the connecting member is made of material which supports the nostril.

8. A nostril dilator according to claim 1, wherein the dilator further comprises an outer protecting layer produced from a printable material.

9. The nostril dilator according to claim 1, wherein the dilator further comprises an outer protecting layer produced from a polyurethane film.

10. A nostril dilator for application to a nose having a longitudinal shape, comprising:

a first nostril holding member and a second nostril holding member, each holding member provided with a first layer of adhesive for temporary adherence to the nostril;

a connecting member for connecting the first and second holding members to each other;

an elastic member extending between the first and the second holding members on a side of the connecting member facing away from the nose and which is connected with its end areas thereto, the elastic member formed by a layer of material which is at least elastic in a longitudinal direction parallel to the longitudinal shape of the nasal dilator, and the elastic member being separate from the connecting member at least in the area between a central transverse area of the nostril dilator and both end areas situated on both sides thereof;

an optical or a physical positioning means for placing the nostril dilator on the nose properly forming a discontinuity in a direction perpendicular to a longitudinal plane of the nostril dilator; and a spacing member positioned between the connecting member and the elastic member keeping these parts spaced wherein at least at the location of a longitudinal center of the nostril dilator the spacing member is provided with a narrow region which is perpendicular to the longitudinal direction of the nostril dilator.

* * * * *